(12) United States Patent
Ikeuchi et al.

(10) Patent No.: US 6,504,032 B1
(45) Date of Patent: Jan. 7, 2003

(54) PROCESS FOR THE PRODUCTION OF 2-PYRIDYLPYRIDINE DERIVATIVES

(75) Inventors: Fumiaki Ikeuchi, Kanagawa (JP); Taichi Shintou, Kanagawa (JP); Hirokazu Suda, Kanagawa (JP)

(73) Assignee: Sankio Chemical Co., Ltd., Tokyo (JP)

( * ) Notice: Subject to any disclaimer, the term of this patent is extended or adjusted under 35 U.S.C. 154(b) by 0 days.

(21) Appl. No.: 10/009,562

(22) PCT Filed: Jun. 13, 2000

(86) PCT No.: PCT/JP00/03831

§ 371 (c)(1),
(2), (4) Date: Dec. 12, 2001

(87) PCT Pub. No.: WO00/76975

PCT Pub. Date: Dec. 21, 2000

(30) Foreign Application Priority Data

Jun. 14, 1999 (JP) .......................................... 11-167308

(51) Int. Cl.[7] ............................................. C07D 213/22
(52) U.S. Cl. ........................................ 546/250; 546/257
(58) Field of Search .................................. 546/250, 257

(56) References Cited

U.S. PATENT DOCUMENTS

4,966,972 A   10/1990   Goe et al.

FOREIGN PATENT DOCUMENTS

| JP | 57-134467 | 8/1982 |
| JP | 64-3169   | 1/1989 |

OTHER PUBLICATIONS

Malm, et al. "Palladium–Catalyzed Coupling of Heteroaryl Alkystannanes with Heteroaryl Halides in the Presence of Silver (I) oxide." Tetrahedron Letters., vol. 33, No. 16, p. 2199–2202 (1992).

Ishikura, et al. "A Novel Synthesis of 4–Aryl– and 4–Heteroarylpyridines via Diethyl (4–pyridyl) borane." Chemical & Pharmaceutical Bulletin., vol. 33, No. 11, p. 4755–4763 (1985).

Gunther R. Pabst et al., The New and Simple 'LEGO' System: Its Application to the Synthesis of Superbranched Oligopyridines, Tetrahedron Letters 39 (1998) pp. 8817–8820.

Oliver C. Pfuller et al., The New and Simple 'LEGO' System for the Synthesis of Thienyl Substituted 2,6–Oligopyridines, Tetrahedron Letters 39 (1998) pp. 8821–8824.

Gunther R. Pabst et al., The New and Simple 'LEGO'0 System: Its Application to the Synthesis of 6 –Oligopyridyl–1,5,12–triazatriphenylenes, Tetrahedron Letters 39 (1998) pp. 8825–8828.

*Primary Examiner*—Patricia L. Morris
(74) *Attorney, Agent, or Firm*—Sughrue Mion, PLLC

(57) ABSTRACT

A process for producing a 2-pyridylpyridine derivative usable as an intermediate for medicines or agricultural chemicals is provided, which does not require expensive metal catalysts, which does not cause environmental problems, and which can be conducted on an industiral scale. The process comprises the step (A) of producing an amidrazone compound from a cyano group-containing heterocyclic compound in water, the step (B) of producing a 1,2,4-triazine compound from the amidrazone compound in water, and the step (C) of producing a 2-pyridylpyridine derivative from the 1,2,4-triazine compound.

9 Claims, No Drawings

PROCESS FOR THE PRODUCTION OF 2-PYRIDYLPYRIDINE DERIVATIVES

TECHNICAL FIELD

This invention provides a process for producing a 2-pyridylpyridine derivative, which is an important intermediate for producing medicines, agricultural chemicals, catalyst ligands, and organic photosensitive materials or dyes for use in electrophotography or electroluminescence elements, in a high yield and with a high purity at a low production cost.

BACKGROUND ART

Various processes for producing 2-pyridylpyridines have been reported. For example, there has been reported a process of condensing a pyridine compound with an N-oxide of a pyridine compound in the presence of Pt— added Pd—C under heating (Yakugaku Zasshi, 99 (12) 1176, 1181 (1979)), but this process provides anendproduct ina low yield. Cross-coupling reaction utilizing Grignard reaction has also been reported (Japanese Patent Laid-Open No. 3169/1989), but this process involves such problems as that a pyridyl iodide compound necessary for obtaining a Grignard reagent for a pyridine is difficult to obtain or synthesize and that special equipment is required. Further, there have been proposed Ullmann condensation reaction between halogenated pyridines (Khim. Geol. Nauk., 114 (1970)) and a process of cross-coupling a halogenated pyridine compound with various metal derivatives in the presence of a Pd catalyst. For example, there have been reported a process of cross-coupling a borane derivative (Chem. Pharm. Bull., 33 (11) 4755 (1985)), (Heterocycles, 23 (9) 2375 (1985)), a process of cross-coupling an alkyltin derivative (Tetrahedron Lett., 33, 2199 (1992)), and a process of cross-coupling a halogenated pyridine compound in the presence of a Ni catalyst (WO9852922).

These processes, however, involve many problems for producing the end product on a large scale. For example, they require extremely expensive catalysts or reagents and require a special treatment for metal-containing waste liquor to be generated. In addition, these reactions produce by-products in a large amount which are extremely difficult to separate, thus products with a purity high enough to be used as intermediates for medicines or electronic materials not having been obtained.

On the other hand, as a process for synthesizing a 1,2,4-triazine using glyoxal, there have been reported a process of acting formamidrazone hydrochloride (Chem. Ber., 101, 3952 (1968)), a process of acting methylthioamidrazone (J. Heterocyclic Chem., 7, 767 (1970)), and an improved process of a process of acting ethyloxalamidrazonate (Synthesis, 5, 351 (1974)), since a process was reported which comprises reacting glyoxal with ethyloxalamidrazonate, then conducting decarboxylation (J. Org. Chem., 31, 1720 (1966)).

In every case, however, glyoxal having a high reactivity yields by-products in large amounts, leading to a low yield. In addition, it requires a special apparatus such as equipment for low temperature and requires a number of steps, thus processes using glyoxal not having been satisfactory as industrial processes.

In addition, it has recently been reported to synthesize a 1,2,4-triazine using a ketone which is less reactive than glyoxal (Tetrahedron Lett., 39, 8817, 8821, 8825 (1998)). However, since this synthesis needs excess hydrazine, a step of removing hydrazine is required, and the substrate is limited to ketones. Thus, the synthesisis applicable only to synthesis of pyridines having a substituent. Accordingly, a process of synthesizing a 2-pyridylpyridine derivative (e.g., 2,4'-dipyridyl, 2,3'-dipyridyl or 2,2'-dipyridyl) via a 1,2,4-triazine using highly reactive glyoxal is so difficult that there have been no reports on the process.

The invention provides a process for producing a 2-pyridylpyridine derivative usable as an intermediate for medicines and agricultural chemicals, which does not require to use expensive metal catalysts, which does not cause environmental problems, and which can be conducted on an industrial scale and, more particularly, it provides a process for producing a 2-pyridylpyridine derivative with an extremely high purity and a high selectivity in a high yield, which can be conducted in a sequential manner at a low production cost.

DISCLOSURE OF THE INVENTION

The objects of the invention can be attained by the following processes.

(1) A process for producing a 2-pyridylpyridine derivative, which comprises:
  (A) a step of producing an amidrazone compound from a cyano group-containing heterocyclic compound in a water solvent;
  (B) a step of producing a 1,2,4-triazine compound from the amidrazone compound in a water solvent; and
  (C) a step of producing a 2-pyridylpyridine derivative from the 1,2,4-triazine compound.

(2) The process for producing a 2-pyridylpyridine derivative as described in (1), wherein the step (A) of producing an amidrazone compound from a cyano group-containing heterocyclic compound comprises reacting the cyano group-containing heterocyclic compound with a hydrazine compound in a water solvent.

(3) The process for producing a 2-pyridylpyridine derivative as described in (1), wherein the step (B) of producing a 1,2,4-triazine compound from the amidrazone compound comprises reacting the amidrazone compound with glyoxal in a water solvent.

(4) The process for producing a 2-pyridylpyridine derivative as described in (1), wherein the step (C) of producing a 2-pyridylpyridine derivative from the 1,2,4-triazine compound comprises reacting the 1,2,4-triazine compound with a 2,5-norbornadiene in a reaction solvent.

(5) The process for producing a 2-pyridylpyridine derivative as described in (1), wherein the amount of water to be used as a solvent in the step (A) of producing an amidrazone compound from a cyano group-containing heterocyclic compound is 0.1 to 10 times by weight the amount of the cyano group-containing heterocyclic compound.

(6) The process for producing a 2-pyridylpyridine derivative as described in (1), wherein the reaction temperature in the step (A) of producing an amidrazone compound from a cyano group-containing heterocyclic compound ranges from 0 to 120° C.

(7) The process for producing a 2-pyridylpyridine derivative as described in (1), wherein the amount of water to be used as a solvent in the step (B) of producing a 1,2,4-triazine compound from the amidrazone compound is 1 to 100 times by weight the amount of the cyano group-containing heterocyclic compound.

(8) The process for producing a 2-pyridylpyridine derivative as described in (1), wherein the reaction temperature in the step (B) of producing a 1,2,4-triazine derivative from the amidrazone compound ranges from 0 to 100° C.

(9) The process for producing a 2-pyridylpyridine derivative as described in (4), wherein the reaction solvent to be used in the step (C) of producing a 2-pyridylpyridine derivative from the 1,2,4-triazine compound is an aromatic hydrocarbon.

The invention is described in more detail below.

In order to describe the invention in more detail, one embodiment of the process of the invention is shown below which, however, does not limit the invention in any way.

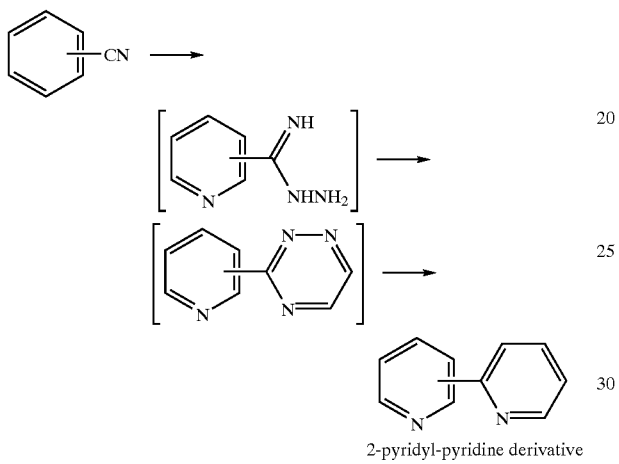

2-pyridyl-pyridine derivative

The invention is a process for producing a 2-pyridylpyridine derivative in a sequential manner from a cyano group-containing heterocyclic compound via an amidrazone compound and a 1,2,4-triazine compound.

Water is used as a solvent in the step of preparing an amidrazone compound from a cyano group-containing heterocyclic compound and the step of preparing a triazine compound from the amidrazone compound in accordance with the invention. In conducting the reaction in the step of preparing an amidrazone compound from a cyano group-containing heterocyclic compound in a water solvent, production of a tetrazine by dimerization of the amidrazone compound is depressed in comparison with the case of using a conventionally proposed solvent and, in addition, a hydrazine need not be used in a large excess amount based on the cyano group-containing heterocyclic compound.

That is, in case where the reaction is carried out using other solvent than water as in the conventional processes, the reaction does not stop at the stage where the amidrazone compound is produced, but further proceeds to produce a tetrazine, a dimer of the amidrazone compound. In addition, a large excess amount of a hydrazine is required. Hence, even where the reaction can be stopped at the stage of production of the amidrazone compound, a large-scale step of removing the hydrazine is required, since the hydrazine will exert detrimental influences on the subsequent step.

In the step of preparing the triazine compound from the amidrazone compound, the triazine compound is obtained in a higher yield by conducting the reaction in a water solvent, without forming by-products such as an osazone compound which is formed as a result of reaction between one mol of glyoxal and two mols of amidrazone compounds and which stops the subsequent reaction, in comparison with the case of using a conventionally proposed solvent. Thus, the end product of 2-pyridylpyridine derivative can be obtained in a high yield.

That is, in the case of conducting the reaction using a solvent other than water as in the conventional art, anosazone compound is highly selectively obtained by the reaction between one mol of glyoxal and two mols of the amidrazone compound, and the intended triazine compound is obtained only in an extremely slight amount, thus the end product of 2-pyridylpyridine derivative being obtained in an extremely slight amount.

First, the step (A) of producing the amidrazone compound from the cyano group-containing heterocyclic compound in awater solvent is described below. Examples of the cyano group-containing heterocyclic compound to be used in the step (A) are illustrated below which, however, are not to be construed as limiting the invention.

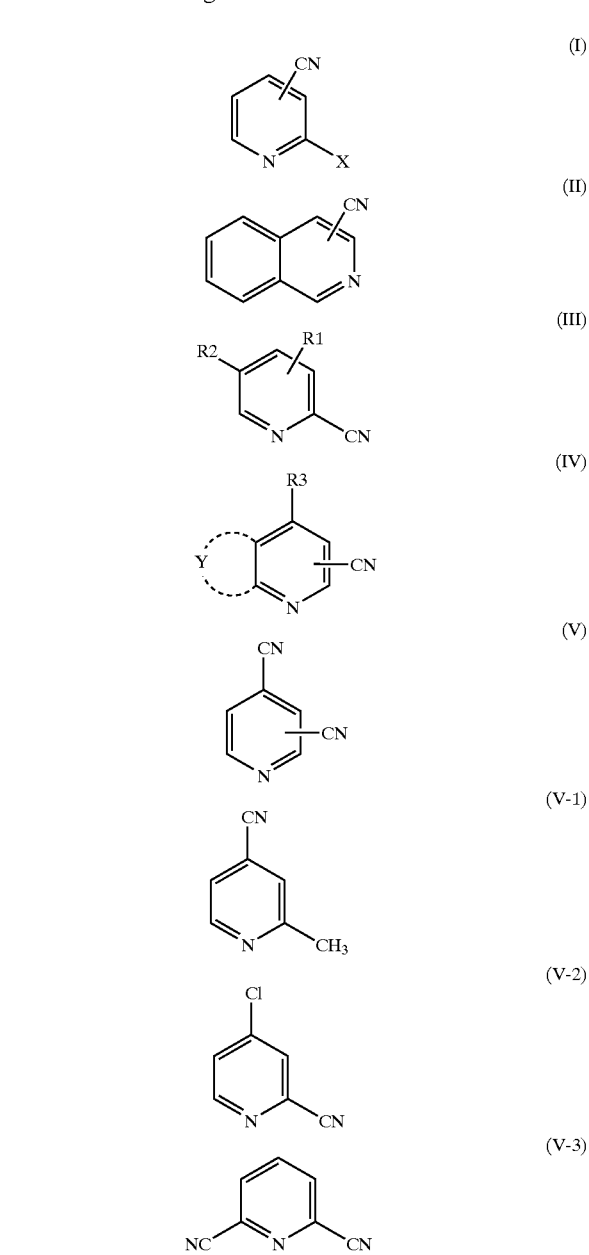

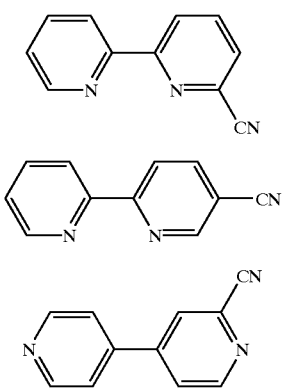

In the above formulae, X represents a hydrogen or a chlorine atom, R1 represents a hydrogen or a methyl group and, when R1 represents a hydrogen atom, R2 represents a chlorine atom, a methyl group or a cyano group and, when R1 represents a methyl group, R2 represents a hydrogen atom, Y represents a condensed cyclohexane ring or benzene ring, R3 represents a hydrogen atom or a cyano group provided that, when Y represents a condensed ring, R3 represents a hydrogen atom.

In the invention, preferred examples of the cyano group-containing heterocyclic compound include 2-cyanopyridine, 3-cyanopyridine, 4-cyanopyridine, 2-cyano-3-methylpyridine, 2-cyano-4-methylpyridine, 2-cyano-5-methylpyridine and 2-cyano-6-methylpyridine, with 2-cyanopyridine, 3-cyanopyridine and 4-cyanopyridine being particularly preferred.

The above-described cyano group-containing heterocyclic compounds may be obtained by converting corresponding carboxylicacids to acidamides, then dehydrating the acidamides or, alternatively, by converting corresponding aldehydes to aldoximes, then dehydrating the aldoximes, according to a conventional manner.

The solvent to be used in the step (A) is water. In case where other solvent than water, such as an alcohol solvent, e.g., methanol, ethanol, 1-propanol or 2-propanol, dimethylformamide (DMF), dimethylsulfoxide (DMSO) or acetic acid is used, a hydrazine compound must be used in a largely excess amount for consuming the starting material. In this case, remaining hydrazine compound would exert detrimental influences on the subsequent step, and hence a large-scale step is required for removing it. In addition, in case where the hydrazine compound is used in a slightly excess amount and the reaction system is heated in order to complete the reaction, the amidrazone compound undergoes further reaction to produce a tetrazine compound, a dimerization product of the amidrazine. Formation of the tetrazine compound prevents one from attaining the objects of the invention. The amidrazone compound may be produced in the absence of any solvent, but solids are formed during the reaction, and stirring the reaction mixture becomes difficult, thus the reaction in the absence of any solvent not being practical.

The water solvent is used in an amount ranging from 0.1 to 10 parts by weight, preferably 0.5 to 5.0 parts by weight, per part by weight of the cyano group-containing heterocyclic compound and, more preferably 1.0 to 2.0 parts by weight in order to prevent stirring failure due to precipitation of solids and complete the reaction in a short time.

In the step (A), it is preferred to react the cyano group-containing heterocyclic compound with the hydrazine compound to thereby prepare the amidrazone compound. The hydrazine compound to be used is not particularly limited but, usually, there are used hydrazine hydrate, hydrazine hydrochloride, anhydrous hydrazine, hydrazine acetate, hydrazine dihydrobromide trihydrate, hydrazine hydrobromide, hydrazine sulfate, hydrazinium chloride, free hydrazine prepared from various hydrazine salts, and the like. Of these, hydrazine hydrate, hydrazine hydrochloride and anhydrous hydrazine are preferred which complete the reaction in a short time and depress formation of by-products, with hydrazine hydrate being more preferred owing to its inexpensiveness and easy handling.

Amount of the hydrazine compound is not particularly limited as long as it is used in a largely excess amount based on the cyano group-containing heterocyclic compound, but may be in a range of 0.50 to 10 mols, preferably 0.80 to 5.0 mols, more preferably 1.0 to 3.0 mols, per mol of the cyano group-containing heterocyclic compound. In case where the cyano group-containing heterocyclic compound has two cyano groups within the molecule, the hydrazine compound is used in an amount two times as much as that described above.

The reaction of the step (A) is conducted at a temperature of usually 0 to 120° C., preferably 20 to 95° C. in view of the problem of solubility of the substrates, more preferably 30 to 70° C for depressing formation of by-products of tetrazines. In conducting the reaction, disappearance of the starting materials is confirmed usually in a period as short as 2 to 5 hours.

Next, the step (B) of producing the 1,2,4-triazine compound from the amidrazone compound is described below. In this step, it is preferred to produce the 1,2,4-triazine compound by reacting the amidrazone compound with glyoxal.

Specifically, water is added to the reaction solution of the former step (A), and glyoxal is added thereto in an amount equimolar with the cyano group-containing heterocyclic compound, followed by heating under reflux, thus the reaction being able to be completed usually in an extremely short period of 1 to 2 hours. In case where hydrazine is used in an excess amount in the preceding step, excess hydrazine is removed before conducting the above-described procedures.

As glyoxal to be used, there are illustrated an aqueous solution of glyoxal, glyoxal di(sodium hydrogensulfite), glyoxal equivalents of 1,4-dioxane-2,3-diol and glyoxal trimeric dihydrate, etc., with an aqueous solution of glyoxal and 1,4-dioxane-2,3-diol being preferred and, in view of inexpensiveness and ease in obtaining and handling, an aqueous solution of glyoxal being more preferred. It is preferred to use glyoxal in an amount equimolar with the cyano group-containing heterocyclic compound because, when the molar amount of glyoxal is more or less than the cyano group-containing heterocyclic compound, there might result a large amount of by-products such as osazone, leading to serious decrease in yield.

The solvent to be used in the step (B) is water. In case where other solvent than water, such as an alcohol solvent, e.g., methanol, ethanol, 1-propanol or 2-propanol, DMF, DMSO or acetic acid is used, 2 mols of the amidrazone compound reacts with 1 mol of glyoxal with a high selectivity to form an osazone compound, thus the intended product of the triazine compound being produced only in an extremely slight amount. Formation of the osazone compound stops the reaction, and hence the end product of the 2-pyridylpyridine derivative is obtained only in an extremely slight amount.

Water is used in an amount of usually 1 to 100 parts by weight per part by weight of the cyano group-containing heterocyclic compound, with 5 to 50 parts by weight being preferred in view of the problem of solubility, and 10 to 30 parts by weight being more preferred.

The reaction of the step (B) is conducted at a temperature of usually 0 to 100° C., preferably 40 to 100° C. in view of the problem of solubility of the substrates, more preferably 60 to 100° C. for completing the reaction in a short period of time. In conducting the reaction, disappearance of the amidrazone compound is confirmed usually in a period as short as 1 to 2 hours.

Next, the step (C) of producing the 2-pyridylpyridine derivative from the 1,2,4-triazine compound is described below.

In the step (C), it is preferred to produce the 2-pyridylpyridine derivative by reacting the 1,2,4-triazine compound with 2,5-norbornadiene.

Specifically, a solvent is added to the reaction solution obtained as described above to extract the reaction product and, after separating the solution, 2,5-norbornadiene is added to the resulting organic layer, followed by heating under reflux. As the solvent, any solvent may be used such as a ploar solvent (e.g., chloroform) or an aromatic solvent having a boiling point of 80° C. or higher. For example, there may be used benzene, toluene, xylene, mesitylene, chlorobenzene, bromobenzene, anisole and dichlorobenzene. Of these, aromatic hydrocarbon solvents having a boiling point higher than that of 2,5-norbornadiene, such as toluene, xylene and mesitylene are preferred, with xylene being more preferred. Alternatively, the reaction solution may be subjected to extraction with an organic solvent such as ethyl acetate before the subsequent reaction and, after concentrating the extract, the solvent may be replaced by the aromatic solvent.

The reaction of the step (C) is conducted at a temperature of usually 60 to 180° C., preferably 80 to 140° C., more preferably 90 to 120° C. In conducting the reaction, disappearance of the 1,2,4-triazine compound is confirmed usually in a period as short as 3 to 5 hours.

After completion of the reaction, the solvent is removed under reduced pressure to concentrate, and the concentrate is distilled or, otherwise, an alcohol or hexane is added to the concentrate to crystallize. Thus, the 2-pyridylpyridine derivative can be obtained with a high purity from the cyano group-containing heterocyclic compound in a sequential manner.

Specific examples of the 2-pyridylpyridine derivative obtained by the invention are illustrated below.

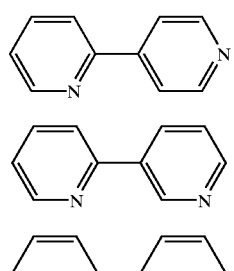

(A-1)

(A-2)

(A-3)

-continued

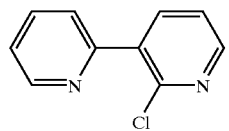

(A-4)

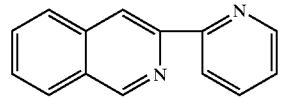

(A-5)

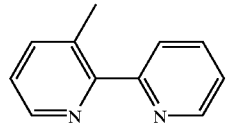

(A-6)

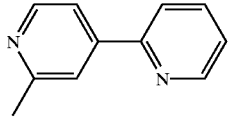

(A-7)

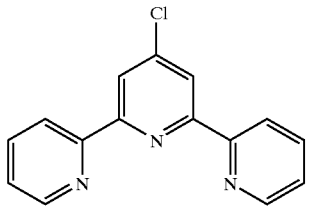

(A-8)

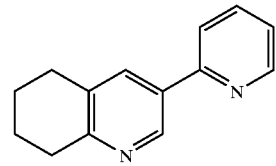

(A-9)

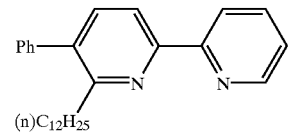

(A-10)

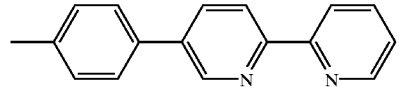

(A-11)

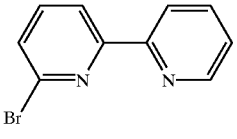

(A-12)

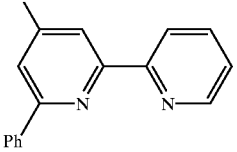

(A-13)

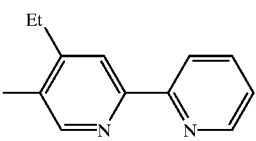

(A-14)

-continued (A-15) 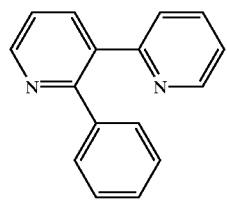

(A-16) 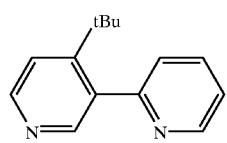

(A-17) 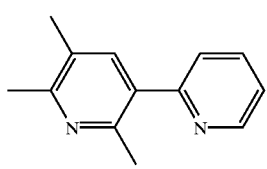

(A-18) 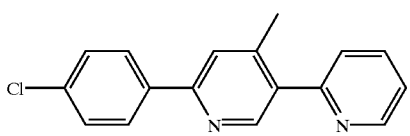

(A-19) 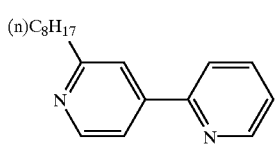

(A-20) 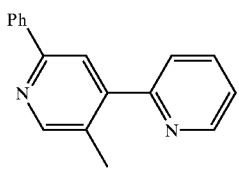

(A-21) 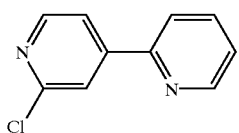

(A-22) 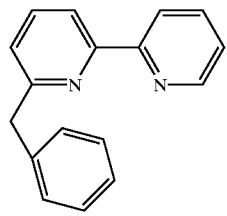

(A-23) 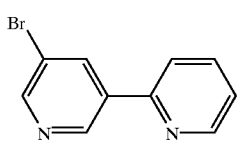

-continued (A-24) 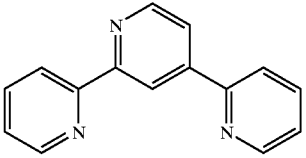

BEST MODE FOR CARRYING OUT THE INVENTION

The invention is now described more specifically by reference to Examples which, however, are not to be construed as limiting the invention. Additionally, purity was determined by high pressure liquid chromatography (abbreviated as "HPLC"). Hereinafter, the term "HPLC analysis" means analysis conducted under the conditions (column: YMC-A-312; detection: UV 254 nm; flow rate: 1.0 ml/min; eluent: acetonitrile/water=25/75 (vol/vol); buffers: 0.2% of acetic acid and 0.2% of triethylamine). Detailed descriptions are given only where the conditions are changed.

EXAMPLE 1

Synthesis of 2,4'-dipyridyl (A-1)

100 ml of water, 100.0 g (0.96 mol) of 4-cyanopyridine and 48.0 g (0.96 mol) of hydrazine hydrate were charged in a 1000 ml 4-necked flask, and reacted at 50° C. for 4 hours under stirring. After confirming disappearance of the starting materials by HPLC analysis, 550 ml of water was further added thereto, and 139 g (0.96 mol) of 40% glyoxal aqueous solution was added thereto, followed by reacting at an outer temperature of 100° C. for 2 hours. After cooling, the reaction solution was subjected to extraction with xylene and separated. 882 g (9.6 mols) of 2,5-norbornadiene was added to the organic layer, and reaction was conducted for 4 hours under refluxing. After completion of the reaction, the organic layer was distilled under reduced pressure of 4.4 to 4.5 Torr to obtain a 134 to 136° C. fraction. Thus, there was obtained 109.3 g (yield: 72.9%) of the end product as pale yellow crystals. HPLC analysis revealed that purity of the product was 99.2%.

EXAMPLE 2

Synthesis of 2,3'-dipyridyl (A-2)

The same synthesis procedures as in Example 1 were conducted except for using 3-cyanopyridine in place of 4-cyanopyridine and, after completion of the reaction, the organic layer was distilled under reduced pressure of 4.9 to 5.0 Torr to obtain a 90 to 93° C. fraction. Thus, there was obtained 127.9 g (yield: 85.3%) of the end product as pale yellow crystals. HPLC analysis revealed that purity of the product was 98.9%.

EXAMPLE 3

Synthesis of 2,2'-dipyridyl (A-3)

The same synthesis procedures as in Example 1 were conducted except for using 2-cyanopyridine in place of 4-cyanopyridine and, after completion of the reaction, the organic layer was distilled under reduced pressure of 1.9 to 2.0 Torr to obtain a 110 to 113° C. fraction. Thus, there was obtained 132.2 g (yield: 88.2%) of the end product as pale yellow crystals. HPLC analysis revealed that purity of the product was 99.3%.

EXAMPLE 4

Synthesis of 2-chloro-5-(2-pyridyl)pyridine (A-4)

The same synthesis procedures as in Example 1 were conducted except for using 2-chloro-5-cyanopyridine and 1,4-dioxane-2,3-diol in place of 4-cyanopyridine and a 40% glyoxal aqueous solution, respectively, and, after completion of the reaction, the organic layer was distilled under reduced pressure of 3.0 to 3.1 Torr to obtain a 150 to 152° C. fraction. Thus, there was obtained 151.0 g (yield: 82.5%) of the end product as pale yellow crystals. HPLC analysis revealed that purity of the product was 99.1%.

EXAMPLE 5

Synthesis of 3-(2-pyridyl)-isoquinoline (A-5)

10 ml of water, 14.8 g (0.096 mol) of 3-cyanoisoquinoline and 5.3 g (0.106 mol) of hydrazine hydrate were charged in a 100 ml 4-necked flask, and reacted at 60° C. for 3 hours. After confirming disappearance of the starting materials by HPLC analysis (following conditions), 55 ml of water was further added thereto, and 13.9 g (0.096 mol) of 40% glyoxal aqueous solution was added thereto, followed by reacting at an outer temperature of 100° C. for 1.5 hours. After cooling, the reaction solution was subjected to extraction with xylene and separated. 88.2 g (0.96 mol) of 2,5-norbornadiene was added to the organic layer, and reaction was conducted for 5 hours under refluxing. After completion of the reaction, the organic solvent was concentrated under reduced pressure and the concentrate was recrystallized from hexane to obtain a 17.9 g (yield: 90.4%) of the end product as pale yellow crystals. HPLC analysis (column: YMC-A-312; detection UV: 254 nm; flowrate: 1.0 ml/min; eluent: acetonitrile/water=50/50 (vol/vol); buffers: 0.2% of acetic acid and 0.2% of triethylamine) revealed that purity of the product was 98.7%.

EXAMPLE 6

Synthesis of 6'-methyl-2,2'-dipyridyl (A-6)

10 ml of water, 11.3 g (0.096 mol) of 2-cyano-6-methylpyridine and 4.8 g (0.096 mol) of hydrazine hydrate were charged in a 100 ml 4-necked flask, and reacted at 50° C. for 3 hours. After confirming disappearance of the starting materials by HPLC analysis, 55 ml of water was further added thereto, and 13.9 g (0.096 mol) of 40% glyoxal aqueous solution was added thereto, followed by reacting at an outer temperature of 100° C. for 2 hours. After cooling, the reaction solution was subjected to extraction with ethyl acetate and separated. After removing the solvent under reduced pressure, 8.82g (0.096 mol) of 2,5-norbornadiene was added to the residue, and reaction was conducted for 3 hours under refluxing. After completion of the reaction, the reaction solution was distilled under reduced pressure of 5.0 mmHg to obtain a 148 to 156° C. fraction. Thus, there was obtained 14.5 g (yield: 89.0%) of the end product as pale yellow crystals. HPLC analysis revealed that purity of the product was 99.2%.

Comparative Examples 1 to 6

In the step of producing the amidrazone compound from the cyano group-containing heterocyclic compound in Example 1, the reaction was conducted by changing the solvent to those shown in the following Table 1. In particular, methanol is the solvent described in the literature (Tetrahedron Lett., 39, 8817 (1998)). Amounts of the reagent used were grouped into two groups; one group being the same as in Example 1, and the other group being those which correspond to theoretical amounts according to the above-described literature. That is, the same procedures as in Example 1 were conducted except for changing the solvent and the amount of hydrazine and, after completion of the reaction, each of the reaction solutions was subjected to HPLC analysis to determine reation ratio. Results thus obtained are shown in Table 1.

TABLE 1

|  | Reaction Solvent | Hydrazine Hydrate (mol) | Relative Yield A (%) | Relative Yield B (%) |
| --- | --- | --- | --- | --- |
| Example 1 | water | 0.96 | 97.2 | 1.1 |
| Com. Ex. 1 | methanol | 0.96 | 30.3 | 28.1 |
| Com. Ex. 2 | ethanol | 0.96 | 33.6 | 22.4 |
| Com. Ex. 3 | DMF | 0.96 | 10.2 | 0 |
| Com. Ex. 4 | DMSO | 0.96 | 13.3 | 0 |
| Com. Ex. 5 | acetic acid | 0.96 | 0 | 0 |
| Com. Ex. 6 | methanol | 9.6 | 10.1 | 70.1 |

In the above Table 1, relative yield A represents relative yield (%) of the end product of amidrazone compound, and relative yield B represents relative yield (%) of the tetrazine compound (impurity) formed by dimerization of the amidrazone compound.

The results of Table 1 apparently show the following.

In the step of producing the amidrazone compound from the cyano group-containing heterocyclic compound, Example 1 gave the end product of amidrazone compound in a higher yield than Comparative Examples 1 to 5 wherein reaction was conducted in a solvent other than water. In these Comparative Examples, the starting material of 4-cyanopyridine remained and, particularly in the case of Comparative Examples 1 and 2 wherein alcohol was used as a solvent, it was observed that the amidra zone compound further reacted with each other to form a dimerized product of a tetrazine compound. In addition, in the case of Comparative Example 6 wherein the amount of hydrazine hydrate was determined based on theoretical amount of hydrazine in the literature, the starting material of 4-cyanopyridine did not disappear completely, and formation of the tetrazine compound was observed. Formation of the tetrazine compound prevents the objects of the invention from being attained. The tetrazine compound in Example 1 was identified by NMR and MS analysis to have the following structure:

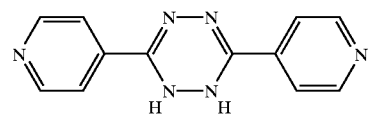

Comparative Example 7

In the step of producing the 1,2,4-triazine compound from the amidrazone compound in Example 1, the reaction was conducted with changing the solvent from water to ethanol as described in the literature (Tetrahedron Lett., 39, 8817 (1998)) and shown in the following Table 2. That is, the same procedures as in Example 1 were conducted except for changing the solvent and, after completion of the reaction, each of the reaction solutions was subjected to HPLC analysis to determine reation ratio. In order to confirm evaluation of the solvents, water was removed by azeotropy with toluene after completion of the reaction in the step of producing the amidrazone compound from the cyan group-containing heterocyclic compound, followed by drying under reduced pressure, and the thus isolated amidrazone compound was used in the step of producing the 1,2,4-triazine compound therefrom. Results thus obtained are shown in Table 2 together with the results of Example 1.

TABLE 2

|  | Reaction Solvent | Relative Yield C (%) | Relative Yield D (%) |
| --- | --- | --- | --- |
| Example 1 | water | 92.1 | 0.2 |
| Com. Ex. 7 | ethanol | 5.4 | 80.4 |

In the above Table 2, relative yield C represents relative yield (%) of the end product of triazine compound, and relative yield D represents yield (%) of the osazone compound (impurity) formed by the reaction between 1 mol of glyoxal and 2 mols of the amidrazone compound.

The results of Table 2 apparently show the following.

In the step of producing the 1,2,4-triazine compound from the amidrazone compound, Example 1 wherein the amidrazone compound was reacted with the amidrazone compound in a water solvent gave the end product of triazine compound in a higher yield than Comparative Example 7 wherein reaction was conducted in ethanol as described in the literature (Tetrahedron Lett., 39, 8817 (1998)). In Comparative Example 7, production of the osazone compound by the reaction between 1 mol of glyoxal and 2 mols of the amidrazone compound precedes, thus the end product of triazine compound being produced only in a slight amount. Formation of the osazone compound prevents one from attaining the objects of the invention. The osazone compound in Example 1 was identified by NMR and MS analysis to have the following structure:

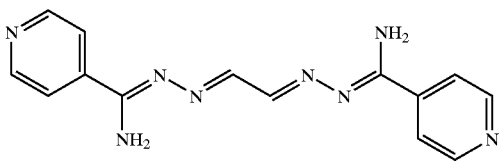

Industrial Applicability

As is apparent from the above Examples and Comparative Examples, the invention provides a process for producing a 2-pyridylpyridine derivative (e.g., 2,4'-dipyridyl, 2,3'-dipyridyl, 2,2'-dipyridyl, etc.) which has conventionally been difficultly synthesized using highly reactive glyoxal via 1,2,4-triazine. That is, by conducting the reaction in a water solvent in the step of preparing the amidrazone compound from the cyano group-containing heterocyclic compound, formation of a tetrazine compound which is a dimerized product of the amidrazone compound is depressed, necessity of using a largely excess amount of hydrazine based on the cyano group-containing heterocyclic compound is eliminated, and the intended amidrazone compound can be obtained with a higher selectivity and a higher reaction ratio, in comparison with the case of using conventionally proposed solvents. In addition, by using a water solvent in the step of preparing the triazine compound from the amidrazone compound, formation of by-products such as an osazone compound formed by the reaction between 1 mol of glyoxal and 2 mols of the amidrazone compound to stop the reaction is depressed, and the triazine compound can be obtained with a higher selectivity and a higher reaction ratio, in comparison with the case of using conventionally proposed solvents. Thus, the end product of 2-pyridylpyridine derivative can be obtained in an extremely high yield. Further, the invention enables to produce the 2-pyridylpyridine derivative from the cyano group-containing heterocyclic group via the amidrazone compound and the 1,2,4-triazine compound in a simple sequential manner. The thus obtained 2-pyridylpyridine derivatives have such a high purity that, in case where they are to be used as imtermediates formedicines, agriculltural chemicals or the like, the 2-pyridylpyridine derivatives can be produced with a high selectivity and a low production cost, thus having an extremely high practicality from industrial viewpoint.

What is claimed is:

1. A process for producing a 2-pyridylpyridine derivative, which comprises:

(A) a step of producing an amidrazone compound from a cyano group-containing heterocyclic compound in a water solvent;

(B) a step of producing a 1,2,4-triazine compound from the amidrazone compound in a water solvent; and (C) a step of producing a 2-pyridylpyridine derivative from the 1,2,4-triazine compound.

2. The process for producing a 2-pyridylpyridine derivative as described in claim 1, wherein the step (A) of producing an amidrazone compound from a cyano group-containing heterocyclic compound comprises reacting the cyano group-containing heterocyclic compound with a hydrazine compound in a water solvent.

3. The process for producing a 2-pyridylpyridine derivative as described in claim 1, wherein the step (B) of producing a 1,2,4-triazine compound from the amidrazone compound comprises reacting the amidrazone compound with glyoxal in a water solvent.

4. The process for producing a 2-pyridylpyridine derivative as described in claim 1, wherein the step (C) of producing a 2-pyridylpyridine derivative from the 1,2,4-triazine compound comprises reacting the 1,2,4-triazine compound with a 2,5-norbornadiene in a reaction solvent.

5. The process for producing a 2-pyridylpyridine derivative as described in claim 1, wherein the amount of water to be used as a solvent in the step (A) of producing an amidrazone compound from a cyano group-containing heterocyclic compound is 0.1 to 10 times by weight the amount of the cyano group-containing heterocyclic compound.

6. The process for producing a 2-pyridylpyridine derivative as described in claim 1, wherein the reaction temperature in the step (A) of producing an amidrazone compound from cyano group-containing heterocyclic compound ranges from 0 to 120° C.

7. The process for producing a 2-pyridylpyridine derivative as described in claim 1, wherein the amount of water to be used as a solvent in the step (B) of producing a 1,2,4-triazine compound from the amidrazone compound is 1 to 100 times by weight the amount of the cyano group-containing heterocyclic compound.

8. The process for producing a 2-pyridylpyridine derivative as described in claim 1, wherein the reaction temperature in the step (B) of producing a 1,2,4-triazine derivative from the amidrazone compound ranges from 0 to 100° C.

9. The process for producing a 2-pyridylpyridine derivative as described in claim 4, wherein the reaction solvent to be used in the step (C) of producing a 2-pyridylpyridine derivative from the 1,2,4-triazine compound is an aromatic hydrocarbon.

* * * * *